US009339237B2

(12) United States Patent
Frix et al.

(10) Patent No.: US 9,339,237 B2
(45) Date of Patent: *May 17, 2016

(54) CONTINUOUS TRANSDERMAL MONITORING SYSTEM AND METHOD

(71) Applicants: James Tyler Frix, Calhoun, GA (US); Andrew Johnson, Athens, GA (US); James Mitchell Frix, Calhoun, GA (US); Robert Andrew Taylor, Anderson, SC (US)

(72) Inventors: James Tyler Frix, Calhoun, GA (US); Andrew Johnson, Athens, GA (US); James Mitchell Frix, Calhoun, GA (US); Robert Andrew Taylor, Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,157

(22) Filed: Jul. 9, 2015

(65) Prior Publication Data
US 2015/0305683 A1    Oct. 29, 2015

Related U.S. Application Data

(63) Continuation of application No. 14/324,963, filed on Jul. 7, 2014, now Pat. No. 9,107,644.

(60) Provisional application No. 61/979,570, filed on Apr. 15, 2014, provisional application No. 61/843,111, filed on Jul. 5, 2013.

(51) Int. Cl.
*A61B 5/02* (2006.01)
*A61B 5/00* (2006.01)
*A61B 5/024* (2006.01)
(Continued)

(52) U.S. Cl.
CPC ............... *A61B 5/721* (2013.01); *A61B 5/0004* (2013.01); *A61B 5/02416* (2013.01);
(Continued)

(58) Field of Classification Search
CPC ........ A61B 5/00; A61B 5/1455; A61B 5/024; A61B 5/74; A61B 5/02416; A61B 5/14551; A61B 5/6824; A61B 5/0004; A61B 5/02433; A61B 5/14552; A61B 5/721; A61B 5/1126; A61B 5/0024; A61B 5/01; A61B 5/0205; A61B 5/021; A61B 5/0537; A61B 5/1118; A61B 5/4809; A61B 2560/0242; A61B 2562/0219

See application file for complete search history.

(56) References Cited

U.S. PATENT DOCUMENTS 7,658,716 B2    2/2010 Banet et al.
8,172,722 B2    5/2012 Molyneux et al.
(Continued)

FOREIGN PATENT DOCUMENTS

DE    102006017970 A1    10/2007
WO    2006079862 A2    8/2006

*Primary Examiner* — Navin Natnithithadha
*Assistant Examiner* — Eric Messersmith
(74) *Attorney, Agent, or Firm* — Smith Tempel Blaha LLC; Matthew T. Hoots

(57) ABSTRACT

Various embodiments of methods and systems for continuous transdermal monitoring ("CTM") are disclosed. One exemplary method for CTM begins by monitoring an output signal from an accelerometer. The accelerometer output signal may indicate acceleration and deceleration of a body part of a user, such as the user's wrist. Based on the accelerometer output signal, it may be determined that the body part of the user has decelerated to a minimum, e.g., substantially zero. With a determination that the body part has decelerated to the minimum, e.g., substantially zero, or has not accelerated beyond the minimum, e.g., substantially zero, the method may determine a reading from a pulse oximeter associated with the accelerometer. Advantageously, the pulse oximetry reading, or a reading from other sensors associated with the accelerometer, may be optimally accurate as motion artifact may be minimized. The pulse oximetry reading may be recorded for later query and/or rendered for the benefit of the user.

20 Claims, 8 Drawing Sheets

(51) Int. Cl.
    *A61B 5/1455* (2006.01)
    *A61B 5/11* (2006.01)
    *A61B 5/01* (2006.01)
    *A61B 5/0205* (2006.01)
    *A61B 5/021* (2006.01)
    *A61B 5/053* (2006.01)

(52) U.S. Cl.
    CPC ........ *A61B 5/02433* (2013.01); *A61B 5/14551* (2013.01); *A61B 5/14552* (2013.01); *A61B 5/6824* (2013.01); *A61B 5/74* (2013.01); *A61B 5/0024* (2013.01); *A61B 5/01* (2013.01); *A61B 5/021* (2013.01); *A61B 5/0205* (2013.01); *A61B 5/0537* (2013.01); *A61B 5/1112* (2013.01); *A61B 5/1118* (2013.01); *A61B 5/1126* (2013.01); *A61B 5/4809* (2013.01); *A61B 2560/0242* (2013.01); *A61B 2562/0219* (2013.01)

(56) References Cited

U.S. PATENT DOCUMENTS

| | | |
|---|---|---|
| 8,253,586 B1 | 8/2012 | Matak |
| 8,289,185 B2 | 10/2012 | Alonso |
| 8,396,687 B2 | 3/2013 | Vock et al. |
| 8,477,046 B2 | 7/2013 | Alonso |
| 2005/0228298 A1 | 10/2005 | Banet et al. |
| 2008/0146895 A1 | 6/2008 | Olson et al. |
| 2009/0227852 A1 | 9/2009 | Glaser |
| 2010/0298683 A1 | 11/2010 | Cabrera et al. |
| 2011/0166491 A1 | 7/2011 | Sankai |
| 2011/0213226 A1 | 9/2011 | Miller et al. |
| 2012/0172679 A1 | 7/2012 | Logan et al. |
| 2012/0221254 A1 | 8/2012 | Kateraas et al. |
| 2013/0125295 A1 | 5/2013 | Krueger |
| 2013/0321168 A1 | 12/2013 | Mahony et al. |
| 2014/0000011 A1 | 1/2014 | Johnson |

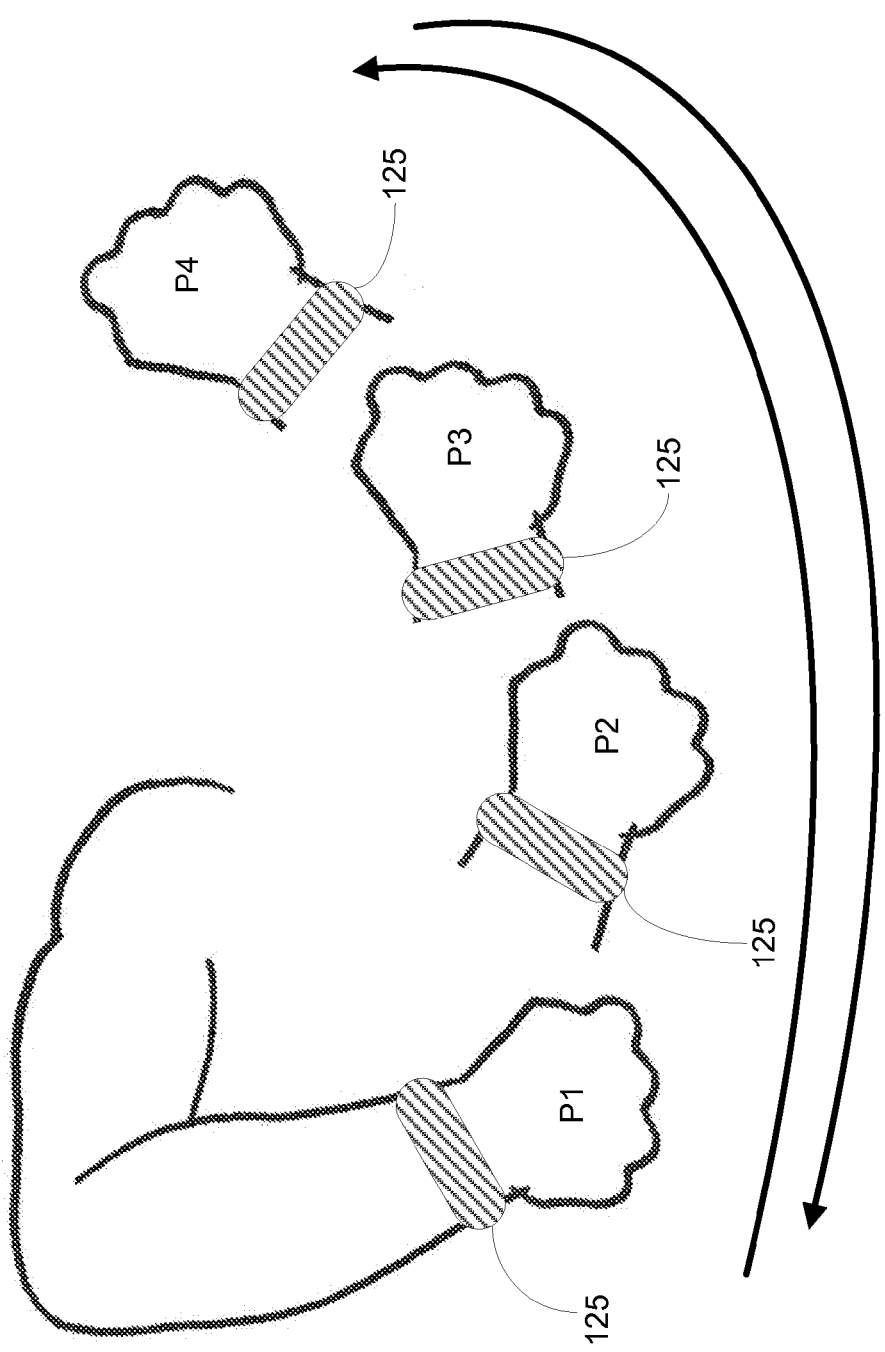

CONTINUOUS TRANSDERMAL MONITORING SYSTEM AND METHOD

BACKGROUND

Pulse oximetry is a technique known in the art for measuring absorbencies in pulsing arterial blood. As one of ordinary skill in the art of pulse oximetry understands, a pulse oximeter may also be used to monitor real time heart rate and arterial oxygen saturation levels.

Pulse oximetry works on the basic concept of light absorption by hemoglobin, the oxygen carrying molecule in red blood cells. Hemoglobin has four oxygen binding sites per molecule. The molecule may absorb a certain amount of light emitted by a pulse oximeter, based on how many of the molecule's oxygen binding sites are bound to an oxygen molecule. The intensity of unabsorbed light sensed by the pulse oximeter may be used to calculate the amount of oxygen bound per hemoglobin molecule. By taking an overall average of these sites, the percentage of the total blood oxygen saturation is calculated.

To accurately monitor light absorption, certain pulse oximeters must be placed on the body in an area where the skin is thin enough for light to pass through yet has enough vascular tissue to generate an acceptable measurement (e.g., ear lobe or tip is an index finger). Certain other pulse oximeters, however, monitor light absorption by measuring the amount of light reflected from a user's body, as opposed to the amount of light that passes through. Reflective pulse oximeters leverage the fact that hemoglobin molecules reflect certain wavelengths of light based on the number of oxygen-binding sites that are bound to oxygen and, as such, may be placed on the body in areas that have dense capillary beds and/or arteries near the skin surface (e.g., underside of the wrist, chest sternum, forehead, etc.).

Notably, pulse oximetry measurements, whether taken with a "pass-through" pulse oximeter or a "reflective" pulse oximeter, are prone to inaccuracies due to electrical noise introduced by user movement. The effect of motion artifact on the accuracy of a pulse oximetry measurement makes pulse oximetry technology known in the art less than ideal for real time pulse oximetry monitoring in users that are moving, such as athletes, runners, etc. Body movement during a reading may provide inaccurate, misleading, or ineffective data. Therefore, there is a need in the art for a system and method that provides an accurate pulse oximetry reading, as well as other physiological calculations and/or combinations of physiological calculations, when a user is in motion.

SUMMARY OF THE DISCLOSURE

The presently disclosed embodiments, as well as features and aspects thereof, are directed towards a system and method for continuous transdermal monitoring that may include measuring pulse oximetry of a subject. The pulse oximetry measurement may be intermittent or it may be by constant measurement. In some embodiments, the method may include measuring the pulse of the subject at a moment during a time interval t, measuring the subject's acceleration at about the moment, and determining whether the pulse measured at the moment is at or about a minimized moment of subject acceleration and/or deceleration.

In an exemplary embodiment, the present disclosure includes a system and method for measuring pulse oximetry of a subject by interval measurement which includes measuring an acceleration or deceleration of a body part of a subject, determining whether the acceleration or deceleration is within a minimum range, and signaling a pulse oximeter to take a pulse oximetry reading.

One exemplary method for continuous transdermal monitoring begins by monitoring an output signal from an accelerometer. The accelerometer output signal may indicate acceleration and deceleration of a body part of a user, such as the user's wrist. Based on the accelerometer output signal, it may be determined that the body part of the user has decelerated to a minimum, e.g., substantially zero. With a determination that the body part has decelerated to substantially zero, or has not accelerated beyond substantially zero, the method may determine a reading from a pulse oximeter associated with the accelerometer. Advantageously, the pulse oximetry reading, or a reading from other sensors associated with the accelerometer, may be optimally accurate as motion artifact may be minimized. The pulse oximetry reading may be recorded for later query and/or rendered for the benefit of the user.

BRIEF DESCRIPTION OF THE DRAWINGS

In the drawings, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral encompass all parts having the same reference numeral in all figures.

FIG. 2A is an illustration of a user's arm motion during running, the wrist of the arm depicted with a sensor package according to a continuous transdermal monitoring ("CTM") embodiment;

DETAILED DESCRIPTION

Figure 1:
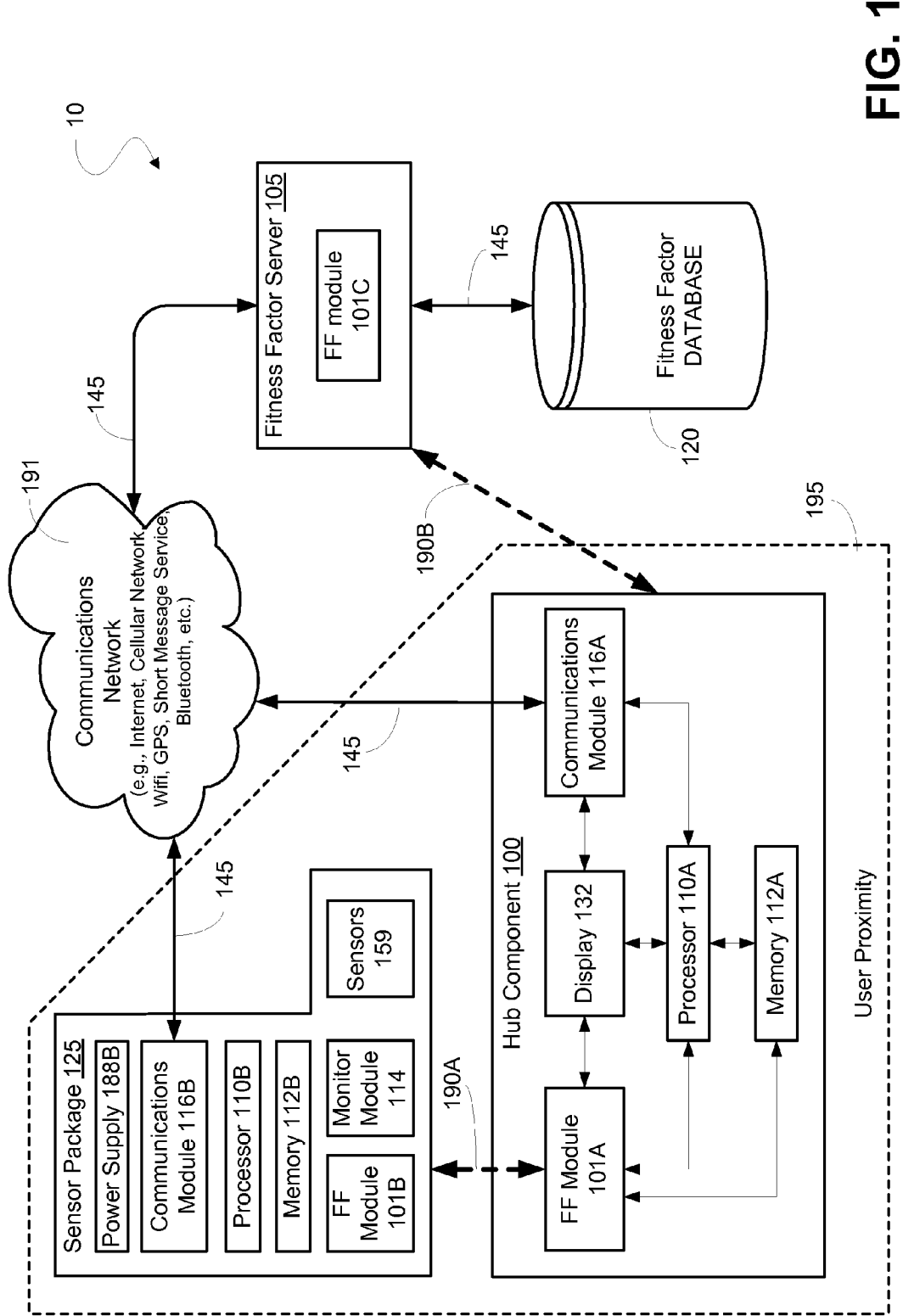
FIG. 1 is a high level functional block diagram illustrating an exemplary architecture of a system for continuous transdermal monitoring ("CTM")

Aspects, features and advantages of several exemplary embodiments of continuous transdermal monitoring ("CTM") systems and methods will become better understood with regard to the following description in connection with the accompanying drawing(s). It will be apparent to one of ordinary skill in the art that the described CTM embodiments provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, any use of absolute terms such as, for example, "will," "will not," "shall," "shall not," "must" and "must not" are not meant to limit the scope of the disclosure as the particular CTM embodiments disclosed herein are merely exemplary.

The word "exemplary" is used herein to mean serving as an example, instance, or illustration. Any aspect described herein as "exemplary" is not necessarily to be construed as exclusive, preferred or advantageous over other aspects.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

In this description, the terms "subject," "patient" and "user" are used interchangeably unless otherwise noted. Specifically regarding the term "user," a user may be a subject or patient to which a sensor package is associated or, in some embodiments, a user may also be a person associated with a hub device and/or a remote server. Notably, a user of a hub device and/or a remote server may also be a user associated with a sensor package.

As used in this description, the terms "component," "database," "module," "system," and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component.

One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet with other systems by way of the signal).

In this description, the terms "central processing unit ("CPU")," "digital signal processor ("DSP")," "graphical processing unit ("GPU")," "processing component" and "chip" are used interchangeably. Moreover, a CPU, DSP, GPU or chip may be comprised of one or more distinct processing components generally referred to as "core(s)."

In this description, the term "portable computing device" ("PCD") is used to describe any device operating on a limited capacity power supply, such as a battery. Although battery operated PCDs have been in use for decades, technological advances in rechargeable batteries coupled with the advent of third generation ("3G") and fourth generation ("4G") wireless technology have enabled numerous PCDs with multiple capabilities. Therefore, a PCD may be a cellular telephone, a satellite telephone, a pager, a PDA, a smartphone, a navigation device, a smartbook or reader, a media player, a combination of the aforementioned devices, a laptop computer with a wireless connection, a remote sensor package worn by a user, among others.

In this description, exemplary embodiments of a continuous transdermal monitoring system are described to comprise a motion sensor in the form of an accelerometer. Notably, specific reference to a motion sensor in the form of an accelerometer is not meant to limit the scope of the disclosure or otherwise suggest that a CTM embodiment must include an accelerometer. For instance, it is envisioned that CTM embodiments that include a motion sensor may, in fact, include an accelerometer but may, alternatively or additionally, include other motion sensing devices such as a gyrometer, a global positioning system ("GPS") or the like. Other devices and combinations of devices for sensing motion other than accelerometers are envisioned. As such, one of ordinary skill in the art will recognize that reference to an accelerometer in this description is for illustrative purposes only and is not meant to suggest that all CTM embodiments must include specifically an accelerometer.

Continuous transdermal monitoring ("CTM") embodiments, as well as features and aspects thereof, are directed towards providing a system and method for measuring pulse oximetry of a subject by constant measurement which may include measuring the pulse of the subject at a moment during a time interval t, measuring the subject's acceleration at or about the moment, and determining whether the pulse measured at or about the moment is at or about a minimized moment of subject acceleration, e.g., a minimum acceleration. Certain CTM embodiments may also monitor via one or more sensors any number of physiological and/or non-physiological parameters associated with the subject including, but not limited to, pulse rate, blood oxygen saturation, transdermal core temperature, Global Positioning System ("GPS") coordinates, 3-axis accelerometer outputs, skin and ambient temperature readings, hydration levels, and barometric readings.

Certain CTM embodiments may include a pulse-oximeter in a sensor package that utilizes reflective, light-absorption technology. The pulse oximeter sensor may be configured to transmit light at two different wavelengths, such as for example 660 nm and 940 nm, through the skin and into an artery of a user. As one of ordinary skill in the art would understand, some of the transmitted light may be reflected and, based on the amount of light reflected and sensed by the pulse oximeter sensor, used to calculate pulse rate and arterial blood oxygen saturation. The sensor package of a CTM embodiment may be placed on the wrist and worn like a wristwatch. Other CTM embodiments may include a sensor package that is integrated into sports equipment such as wristbands, sweatbands, braces, shoulder pads, helmets, mouthpieces, etc. By having a durable encasement and a monitoring system that accounts for movement, the circuitry within the sensor package, and the integrity of the data it generates, may be protected from impact and movement.

It is envisioned that a sensor package of a CTM embodiment may be placed on the body of a user over any artery or arterial bed, such as the forehead, ear, bicep, ankle, etc. As such, the particular location of a sensor package, as applied to a user, will not limit the scope of a CTM embodiment. For example, in a football application, the sensor package may be implanted into the front of a player's helmet and targeted at the forehead, or integrated into the player's shoulder pads right over the sternum. Both the forehead and the sternum offer superficial arterial beds that may present an opportunity to yield good accuracy in reflective pulse oximetry measurement, as would be understood by one of ordinary skill in the art of pulse oximetry. As another example, in an application for use by a patient in a hospital, it is envisioned that the sensor package of a CTM embodiment may be worn on the wrist or ankle for ease of use.

A CTM embodiment may include components in addition to a pulse oximeter to track a user's motion and surrounding environment. For example, it is envisioned that a CTM embodiment may include a GPS sensor and accelerometer for monitoring movement, distance, velocity, and acceleration of the user. Moreover, some embodiments may include combinations of a barometer, skin and ambient temperature probe, core temperature sensor, and a hydration sensor for monitoring a user's elevation during a workout, ambient temperature exposure, skin temperature and sweat-fluid composition along with the athlete's core body temperature. Certain embodiments may also include a UV sensor for monitoring the user's sun exposure. Using one or more readings generated by the sensors, a user's blood pressure may be estimated using linear regression. The accelerometer may also be used to determine the amount of time the user sleeps by tracking movement. All of these readings may be taken in real time and relayed wirelessly to a portable computing device, or other computing device, such as a Smartphone or computer.

Certain CTM embodiments may include an integrated light emitting diode ("LED") screen which may render continuous information to the user of the CTM embodiment. A CTM embodiment may be equipped with programmable alarms that may sound if any reading recognized by the sensor package falls outside of a desired, preset range. Notably, it is envisioned that certain CTM embodiments may leverage a single computing device, or "hub" device, in communication with two or more sensor packages, thereby providing for a single user to monitor several other users associated with a sensor package.

It is envisioned that some CTM embodiments may include a hub device, such as a portable computing device that is communicatively linked to one or more sensor packages using Bluetooth or another short wave radio signal. Certain CTM embodiments may store data collected by a sensor package, output data to a user in real time, transmit collected data to a remote device such as a server, or any combination thereof. The collected data may be leveraged by certain CTM embodiments to generate a general fitness factor from a weighted computation of multiple sensor outputs. It is envisioned that the fitness factor output may be generated by algorithms that are customized by the user such that certain data inputs are weighted according to user selection.

In exemplary CTM embodiments, the fitness factor may be calculated from an algorithm based on data gathered from one or more studies that quantify various heart rate levels during and after exercise. A user's core temperature reading taken in correlation with the heart rate readings, along with other physiological readings from a sensor package such as blood pressure and oxygen saturation, may contribute to calculation of a fitness factor according to a fitness factor algorithm in a CTM embodiment. Moreover, individual metrics such as metabolic expenditure, resting heart rate, maximum heart rate, gender, age, heart rate variability, heart rate recovery, height, weight, and other metrics may also be tracked and incorporated into the fitness factor in some embodiments.

As described above, it is envisioned that a fitness factor may be calculated based on a statistically verified weighted scoring system composed of the various health metrics input by a user and/or monitored and tracked by a sensor package/hub device. The software package may generate data that may inform a care-giver or patient or athlete about a general fitness level, thus allowing a user to customize activities. For instance, a football team using a CTM embodiment may determine how demanding practice should be for a given week based on the players' average fitness level according to outputs generated by a fitness factor algorithm. Similarly, a fitness factor algorithm according to a CTM embodiment may provide an individual user with a unitless output against which to measure improvement of a general physical fitness level.

A CTM embodiment may feature onboard memory storage as well as a wireless transmitter in order to store and/or send real time output data. The antenna for the wireless transmitter and the printed circuit board may be flexible and embedded along the curvature of a component of the CTM embodiment, such as a sensor package. As previously described, a sensor package component of a CTM embodiment may include any number of onboard sensors including, but not limited to, a 3-axis accelerometer, GPS receiver, barometer, ambient and skin temperature gauges, hydration sensor, core body temperature sensor and a reflective pulse-oximeter. Notably, any combination of the sensors may reside within a sensor package and/or a hub device of a CTM embodiment.

Certain CTM embodiments may include algorithms for collecting accurate pulse oximetry readings, as well as other sensor readings, by minimizing the effects of motion artifact errors when the reading(s) is taken. An exemplary algorithm involves measuring when user motion and/or movement is at a minimum. Based on a preset input defining what constitutes minimum movement, readings from an accelerometer and/or other methods of position measurement may be used to recognize when user movement is at a minimum. Consequently, a CTM embodiment may recognize readings taken from other sensors at a point in time that is close to the time of minimal user movement as being accurate. In such an embodiment, for example, an accelerometer in a sensor package may be effectively functioning as the on/off control for the oximeter sensor, i.e. the accelerometer output may trigger the pulse oximeter sensor to take a reading when user movement is at a minimum, and vice versa.

A pulse oximeter included in a sensor package component of a CTM embodiment may comprise a red LED that may be pulsed for approximately 50 microseconds then turned off Subsequently, after 450 more microseconds an infrared LED may be pulsed for approximately 50 microseconds then turned off After 450 more microseconds, the red LED may be turned back on and the cycle may repeat. The duration of the pulse oximeter cycle may be programmable and therefore subject to change in some CTM embodiments. Once the light generated by the LEDs is reflected off of an artery or artery bed of a user, it may be absorbed by a photodiode which may emit a small current of a few micro amps, as would be understood by one of ordinary skill in the art. The current may be sent to a transimpedance amplifier, sometimes referred to as an op-amp, which may convert the few micro-amps of current into a few millivolts, as is understood by one of ordinary skill in the art of electronics. The signal may then be sent to a bandpass pass filter that may filter out all the noise above 5 Hz and below 0.5 Hz. This may allow a pulse rate resolution of as low as 20-30 beats per minute and as high as 300 beats per minute in some CTM embodiments. It is envisioned that a bandpass filter width may be adjusted or modified to achieve various, or a range of, resolutions. From there, the voltage may be passed through a gain amplifier. The gain amplifier may set a gain and DC offset in order to properly set the voltage's output signal level equal to the microcontroller's ADC range, as would be understood by one of ordinary skill in the art of electronics. Once that is accomplished, it may be sent through an analog to digital converter ("ADC") and into a microcontroller.

As described above, a sensor package component in a CTM embodiment may include a hydration sensor, reflective pulse co-oximeter, and/or a core body temperature sensor. The hydration sensor may be comprised of two electrodes with a potentiometer attached. Based on the amount of current conducted between the electrodes, the electrolyte concentration in the user's sweat may be calculated, as would be understood by one of ordinary skill in the art. This data may be used by a CTM embodiment to determine the user's overall hydration and electrolyte levels. If a single electrolyte needed to be targeted, such as sodium for example, an electrolyte specific electrode may be used, such as a sodium-selective ion electrode.

A pulse co-oximeter included in a CTM embodiment may function in almost the same way as the reflective pulse oximeter described above. A pulse co-oximeter may send several different wavelengths of light through an arterial bed in order to distinguish oxyhemoglobin from carboxyhemaglobin, as would be understood by one of ordinary skill in the art. As such, a CTM embodiment that includes a co-oximeter in the sensor package may provide for the calculation of a user's total hemoglobin count. Notably, a hemoglobin count may provide the basis for intervention, e.g., an early warning to massive bleeding or other traumatic events.

A core body temperature sensor included in the sensor package of a CTM embodiment may also leverage reflective technology. Water absorption rates in the near infrared spectrum are sensitive to temperature changes. As temperature increases, water's absorption, over these near infrared wavelengths, undergoes a blue-shift and narrows while increasing in intensity. By tracking these shifts with diffuse optical spectroscopy, a CTM embodiment may calculate a spectral arterial temperature representative of a user's core body temperature.

Physiological and non-physiological data monitored, tracked and collected by a sensor package of a CTM embodiment may be transmitted to a hub device if present, such as a portable computing device in the form of a Smartphone with an associated CTM application or a remoted server with associated software. The hub device may receive the data via a wireless transmission and then sort it into an array that compartmentalizes the data based upon the source of the data, i.e the GPS transceiver, accelerometer, barometer, etc. Next, the data may be processed by a CTM algorithm that calculates the arterial oxygen saturation, instantaneous velocity, distance traveled, G-force, ambient and skin temperature, heart rate, acceleration, core temperature, blood pressure, and/or general fitness level of a user. Notably, it is envisioned that the collected data and/or outputs generated by the collected data may be rendered to a user according to a preferred format.

The one or more integrated circuits and components of a given CTM embodiment may be protected with a hard plastic covering. It is envisioned that an outer band housing all, or a portion of, a sensor package may be worn by a user and may also be made of a protective material such as neoprene, flexible plastic, rubber, or some other type of flexible and protective fabric. One or more components in a CTM embodiment may feature a strap or some other means to tighten the embodiment down in order to prevent and/or limit movement or slippage relative to a user's person. Any component may also be made elastic or form fitting to possibly eliminate the strap. For instances when one or more components of a CTM embodiment is integrated into sports equipment, it is envisioned that the electronics may be protected by that equipment. A helmet may have the device imbedded into the padding over the forehead, and a wrist or ankle brace/guard may have the device sewn into the fabric and protected by the brace or guard itself, for example. A mouthpiece may be designed with the device molded into it, as could an earpiece perhaps used for communication between teammates. Integration into any and all possible sports equipment is envisioned.

Exemplary CTM embodiments, as well as features and aspects thereof, are directed towards providing a system and method for measuring pulse oximetry of a subject by constant measurement which includes measuring the pulse of the subject at a moment during a time interval t, measuring the subject's acceleration at about the moment, and determining whether the pulse measured at the moment is at or about a minimized moment of subject acceleration.

In an exemplary embodiment, a CTM algorithm begins at beginning time t. A pulse oximeter may be attached to the subject at a convenient point of its body and the pulse oximeter may take readings at either predefined intervals or, in another embodiment, intervals dependent on the movement of the subject.

An accelerometer attached to the patient or user, which accelerometer is proximate to the pulse oximeter, may take readings at or about the same moment the pulse oximeter takes readings. The term "at or about the same" may mean substantially simultaneous, or from about 1 to about 10 milliseconds, or from about 1 to about 5 milliseconds, or from about 1 to about 3 milliseconds, depending on the particular CTM embodiment. The readings of the pulse oximeter and the accelerometer are correlated by the moments of reading over time interval t.

The moments of minimized acceleration are selected and the correlated pulse oximetry readings are selected. The selected moments of pulse oximetry are then used to determine the oxygen levels of the subject during time interval t and those oxygen levels are used for further evaluation of the subject.

An exemplary system and method for measuring pulse oximetry of a subject by measurement at minimized movement points includes measuring an acceleration of a subject, determining whether the acceleration is within a minimum range, and signaling a pulse oximeter to to take a subject pulse oximetry reading if the acceleration is within the minimum range.

In an exemplary embodiment, a pulse oximeter may be attached to the subject at a convenient point of its body. An accelerometer attached to the patient, which accelerometer is proximate and in communication with the pulse oximeter, make take readings. The accelerometer reading may be compared to a predefined set of minimized accelerometer readings. If the accelerometer falls within the range, then the accelerometer signals the pulse oximeter to take a reading, and the reading may be transmitted to a data storage module or software module.

In another exemplary embodiment, the accelerometer reading and the pulse oximetry reading are substantially correlated such that they are read at substantially simultaneous points in time, or from about 2 to about 20 milliseconds, or from about 2 to about 10 milliseconds, or from about 1 to about 3 milliseconds, depending on CTM embodiment.

In certain CTM embodiments, it is envisioned that the underside of the wrist may provided superficial vasculature from the radial and ulnar artery. In these embodiments, it is envisioned that more accurate pulse oximetry measurements may be taken during tachycardia, e.g., at high pulse rates (for example, at pulse rates at or greater than about 100 beats per minute to about 250 beats per minute), as compared to other sites. In another embodiment, the accelerometer and/or the pulse oximeter may be positioned on or about the top side of the wrist when during brachicardia, e.g., at low pulse rates (for example at pulse rates at or lower than 60 beats per minute), more accurate readings may be attainable.

In another CTM embodiment, there may be provided a method of determining a General Fitness Factor (referred to in the present description as "GFF" or "FF") using, in whole or in part, the methods of pulse oximetry measurements described herein. The GFF may be determined using an algorithm that objectively calculates fitness based on weighted inputs of physiological and/or non-physiological inputs and quantifies the data in a single unitless number.

In an exemplary CTM embodiment that generates a fitness factor, the GFF may enable physicians, trainers, and even individuals to track fitness in a simple and effective manner. The algorithm may be customizable and may comprise inputs from a motion-tracking device, including but not limited to a global positioning system ("GPS"), an accelerometer, and gyrometer along with a continuous heart rate monitor as well as data from other sources such as a skin temperature gauge or breathing apparatus.

Utilizing these technologies, objective, unique, and specific fitness data may be captured, enabling a CTM algorithm to calculate a quantified fitness factor value using objective data associated with physiological and/or non-physiological parameters including, but not limited to, resting heart rate (HR), maximum heart rate (MHR), projected maximum heart rate (PMHR), heart rate variability (HRV), heart rate recovery (HRR), and movement profile (MP). In some embodiments, it is envisioned that the only user inputs may be age, height, and weight. It is envisioned that weighted combinations of such objective data associated with physiological and/or non-physiological parameters may be used by CTM embodiments to generate a fitness factor.

HR may mean the number of times a heart beats during a given time frame while an individual is not moving. For instance, if the heart beats 200 times over a three-minute span, the HR is 67. MHR may mean the maximum heart rate reached during a time of physical activity. PMHR may mean the projected maximum heart rate for an individual based on age and is equal to (220—subject age). HRV may mean the standard deviation of heart rate during a period of physical exertion. HRR may mean the time span between the end of a period of physical exertion and when heart rate returns to resting heart rate levels. MP may mean the movement during physical exertion correlated to the time taken to perform the movement.

In a certain embodiment, MP may be measured from the moment when the heart rate rises above resting levels over a short period of time, which may be between 1 and 20 seconds, and may end when the heart rate returns to a resting level. MP may take into account how long a person is in motion and how much exertion occurs during that movement (depicted by MHR). This aids in distinguishing the type of movement occurring, for example, whether the movement be a 100-yard sprint, a pull-up, or a three-mile run.

For example, a CTM algorithm may calculate a weighted summation of the various inputs. Each of the analyzed inputs may be recognized by the user as not having an equal effect on determining the user's physical fitness. For instance, HRR may be considered a dominant predictor of fitness, while age may not be considered a strong indicator of fitness. In addition, some inputs may have an inverse correlation with fitness levels, such as HR, and these inputs may be weighted to reflect the negative association. As a result, each of the inputs may be assigned a contributory weight to the final quantitative number. The total contribution may then be divided by a constant to get the final Fitness Factor to fall on a certain scale such as from 1 to 10 or even 1 to 1000, for example.

For example, a fitness factor calculation, adjusted by a constant to fit on a scale 1 to 100 may be generated from an exemplary CTM algorithm in the following manner:

|  | Data | Weight | Contribution |
| --- | --- | --- | --- |
| Age | 24 | 1 | 24 |
| Height (inches) | 60 | 0.5 | 30 |
| Weight (pounds) | 110 | 0.363636364 | 327.2727273 |
| Resting HR | 50 | 4 | 200 |
| Predicted Maximum HR | 186 | 1 | 186 |
| Maximum HR during workout | 160 | 1 | 160 |
| HR Recovery (seconds) | 500 | 0.02 | 200 |
| Heart Rate Variability (HRV) | 10 | 10 | 10 |
| Movement Profile (MP) | 120 | 1 | 120 |
| Total |  |  | 1257.272727 |
| Fitness Factor |  |  | 62.86363636 |

Moreover, the algorithm may continue to adapt to the subject and learn its movement habits to better tailor a movement profile. The algorithm may further comprise a kernel consisting of a moving average over a given time frame. In addition, the calculation may be adjusted to fit a certain scale, such as from 1 to 10 or even 1 to 1000.

An exemplary CTM embodiment running an algorithm for generating a fitness factor of a subject, with age, height, weight, and resting heart rate known, begins at a certain time. For a time i, the exemplary algorithm measures pulse oximetry from the beginning of physical exertion to the end. Pulse oximetry readings may be taken according to the algorithms described herein. Total heart rate and accelerations may be recorded over time i. At the end of time i, the time interval until resting heart rate resumes may be recorded and HRR may be calculated. The algorithm may then calculate HR, MHR, PMHR, HRV, HRR, MP and GFF.

Turning now to FIG. 1, illustrated is a high level functional block diagram of an exemplary architecture of a system 10 for continuous transdermal monitoring ("CTM"). A user proximity 195 includes a hub component 100 in the form of a portable computing device and a sensor package 125. The user proximity 195 envisions a sensor package 125 in wireless communication via link 190A with a hub component 100 that is in the vicinity of a user. For example, a user wearing a sensor package 125 and carrying a portable computing device 100, such as a Smartphone, on his person would be one example of the hub component 100 and the sensor package 125 being within the user proximity 195. Another example of the hub component 100 and the sensor package 125 being within the user proximity 195 would include the sensor package 125 being worn by an athlete on a field of play and the hub component 100 being monitored by a trainer on the sidelines.

Notably, although the FIG. 1 illustration depicts a sensor package 125 and a hub component 100 within a common user proximity 195, it will be understood that not all embodiments of a CTM system and method require a hub component 100 and a sensor package 125 to be within a user proximity. That is, it is envisioned that certain functionality in a CTM embodiment may be implemented via a remote computing device such as a fitness factor server 105. In such embodiments, the sensor package 125 may communicate with the fitness factor server 105 via a communications network 191 without need to communicate 190A with a hub device 100. In other embodiments, a sensor package 125 may communicate with either or both of the fitness factor server 105 and the hub component 100. Similarly, in some embodiments, the hub component 100 may transmit data to and/or from the fitness factor server 105 via link 190B which is implemented over communications network 191.

In the FIG. 1 illustration, the sensor package 125 is shown to include a power supply 188B for powering the sensor package 125, a communications module 116B for establishing communications with either or both of hub component 100 and fitness factor server 105 via communications network 191, a processor 110B and a memory 112B. The sensor package 125 also is shown to include sensors 159 (such as may include any combination of a pulse oximeter, a co-oximeter, a core body temperature sensor, an ambient temperature sensor, an accelerometer, a GPS transceiver, etc.), monitor module 114 for monitoring the sensors 159 and fitness factor ("FF") module 101B for processing physiological and/or non-physiological readings from sensors 159 according to CTM algorithms.

Similar to the sensor package 125, the hub component 100 includes a communications module 116A for transmitting and/or receiving communications over network 191 from fitness factor server 105 and/or sensor package 125, a processor 110A, a memory 112A and an FF module 101A. The hub component 100 also is shown to include a display 132 for rendering one or more outputs to a CTM user. The fitness factor server 105 is also depicted as including an FF module 101C.

Notably, not all of the components depicted in the FIG. illustration are required in all CTM embodiments. That is, it is envisioned, for example, that a certain CTM embodiment may include just a single FF module 101A in a hub component while other embodiments include FF modules 101 in each of the sensor package 125, the hub component 100, and/or the fitness factor server 105. As such, it will be understood from the FIG. 1 illustration that all of certain module, or a portion of a certain module, may or may not reside in a certain component of a CTM system.

As described above, the sensor package 125 may be worn by a user such that sensors 159 monitor certain physiological and/or non-physiological parameters associated with the user. Notably, although not shown in the FIG. 1 illustration, it is envisioned that certain sensors, such as ambient temperature sensors, may reside within hub component 100 in some embodiments. The monitor module 114 monitors the sensors and forwards the collected data to the FF module 101B according to instructions dictated by the FF module 101B. For example, the FF module 101B may receive accelerometer readings from an accelerometer in sensors 159 and, based on the accelerometer readings, determine that the sensor package 125 is stable in motion. The FF module 101B may subsequently instruct the monitor module 114 to record and forward a pulse oximetry reading.

The data generated by the sensors 159, collected by the monitor module 114 and managed by the FF module 101B may be stored locally in the memory 112B of the sensor package 125 and/or transmitted to the hub component 100 and/or the fitness factor server 105. Once received by the hub component 100 and/or the fitness factor server 105, the FF modules 101A, 101C may use the data to generate other CTM outputs such as a fitness factor. Notably, it is envisioned that certain CTM embodiments may be comprised completely within a sensor package 125, while other CTM embodiments may utilize a very streamlined sensor package 125 including only those components needed for collecting sensed data and transmitting to other components in the system.

In certain CTM embodiments, data generated by sensors 159 and transmitted to fitness factor server 105 may be stored in a database 120 for later download and utilization. Similarly, it is envisioned that either or both of sensor package 125 and hub component 100 may include a fitness factor database 120 in their respective memories 112.

The exemplary embodiments of a hub component 100 and sensor package 125 envision remote communication, real-time software updates, extended data storage, etc. and may be leveraged in various configurations by users of system 10. Advantageously, embodiments of hub components 100 and/or sensor packages 125 configured for communication via a computer system such as the exemplary system 10 depicted in FIG. 1 may leverage communications networks 191 including, but not limited to cellular networks, PSTNs, cable networks, WiFi and the Internet for, among other things, software upgrades, content updates, database queries, data transmission, etc. Other data that may be used in connection with a hub component 100 and/or sensor package 125, and accessible via the Internet or other networked system, will occur to one of ordinary skill in the art.

The illustrated computer system 10 may comprise a fitness factor server 105 that may be coupled to a network 191 comprising any or all of a wide area network ("WAN"), a local area network ("LAN"), the Internet, or a combination of other types of networks. It will be understood that the term server 105 may refer to a single server system or multiple systems or multiple servers. The server 105 may be coupled to a fitness factor database 120, as described above. The fitness factor database 120 may store various records related to, but not limited to, historical sensor reading data, fitness factor algorithms, filters/rules algorithms, user preferences, previously calculated fitness factors, trends, etc.

When the server 105 is coupled to the network 191, the server 105 may communicate through the network 191 with various different hub components 100 and sensor packages 125 associated CTM users. Each hub component 100 and/or sensor package 125 may run or execute web browsing software or functionality to access the server 105 and its various CTM applications including FF module 101C. Any device that may access the network 191 either directly or via a tether to a complimentary device, may be a hub component 100 or sensor package 125 according to the computer system 10. The hub component 100 or sensor package 125, as well as other components within system 10 such as, but not limited to, a wireless router (not shown), may be coupled to the network 191 by various types of communication links 145. These communication links 145 may comprise wired as well as wireless links. The communication links 145 allow a hub component 100 or sensor package 125 to establish virtual links 190 with the server 105 and/or each other. While a virtual link 190B, for example, is depicted between the server 105 and the hub device 100, an actual wired or wireless link 145 may exist between the server 105 and the hub device 100. This link 145 may only be used to relay data to the FF server 105 from hub component 100 or sensor package 125, depending on embodiment, as a uni-directional communications channel. In other exemplary embodiments, the FF server 105, hub component 100 and/or sensor package 125 may establish bi-directional communications over network 191 as understood by one of ordinary skill in the art.

As shown, the hub component 100 may include a display 132, a processor 110A and a communications module 116A that may include one or more of a wired and/or wireless communication hardware and a radio transceiver 117. It is envisioned that the display 132 may comprise any type of display device such as a liquid crystal display ("LCD"), a plasma display, an organic light-emitting diode ("OLED") display, a touch activated display, and a cathode ray tube ("CRT") display, a brail display, an LED bank, and a segmented display. A hub component 100 may execute, run or interface to a multimedia platform that may be part of a plug-in for an Internet web browser.

The communications modules 116 may comprise wireless communication hardware such as, but not limited to, a WiFi card or NFC card for interfacing with FF module 101. Further, the communications modules 116 may include a cellular radio transceiver to transmit collected physiological and/or non-physiological data as well as other information to other components, as depicted in the system 10 embodiment. One of ordinary skill in the art will recognize that a communications module 116 may include application program interfaces to processor 110.

It is envisioned that a hub component 100 and/or sensor package 125 may be configured to leverage the cellular radio transceiver of the communications modules 116 to transmit data, such as physiological data by way of a secure channel using wireless link 190. Communication links 145, in general, may comprise any combination of wireless and wired links including, but not limited to, any combination of radio-frequency ("RF") links, infrared links, acoustic links, other wireless mediums, wide area networks ("WAN"), local area networks ("LAN"), the Internet, a Public Switched Telephony Network ("PSTN"), and a paging network.

An exemplary hub component 100 and/or sensor package 125 may also comprise a computer readable storage/memory component 112 for storing, whether temporarily or permanently, various data including, but not limited to, physiological readings and fitness factor calculations.

FIG. 2A is an illustration of a user's arm motion 11 during running, the wrist of the arm depicted with a sensor package 125 according to a continuous transdermal monitoring ("CTM") embodiment. As can be seen in the FIG. 2A illustration, and as would be understood by one of ordinary skill in the art of running, a user's arm may translate back and forth between a forwardmost point P4 and a rearmost point P1 as the user runs. As would further be understood by one of ordinary skill in the art of running, the user may be gliding above a running surface, with neither foot in contact with the running surface, when the arm of the user is at the forwardmost and rearmost points P4 and P1, respectively. Additionally, and as would be understood by one of ordinary skill in the art of running, the user's arm may accelerate and then decelerate as it moves from position P1 to P2 to P3 to P4. Similarly, the user's arm may accelerate and then decelerate as it moves from position P4 to P3 to P2 to P1. Advantageously, therefore, with no body part of the runner in contact with the running surface, and the arm of the runner at a momentarily stationary position as it decelerates to a minimum, e.g., substantially zero, acceleration before it reverses its direction of motion (points P1 and P4), a CTM embodiment may take a pulse oximetry reading with minimal noise attributable to motion artifact.

Figure 2B:
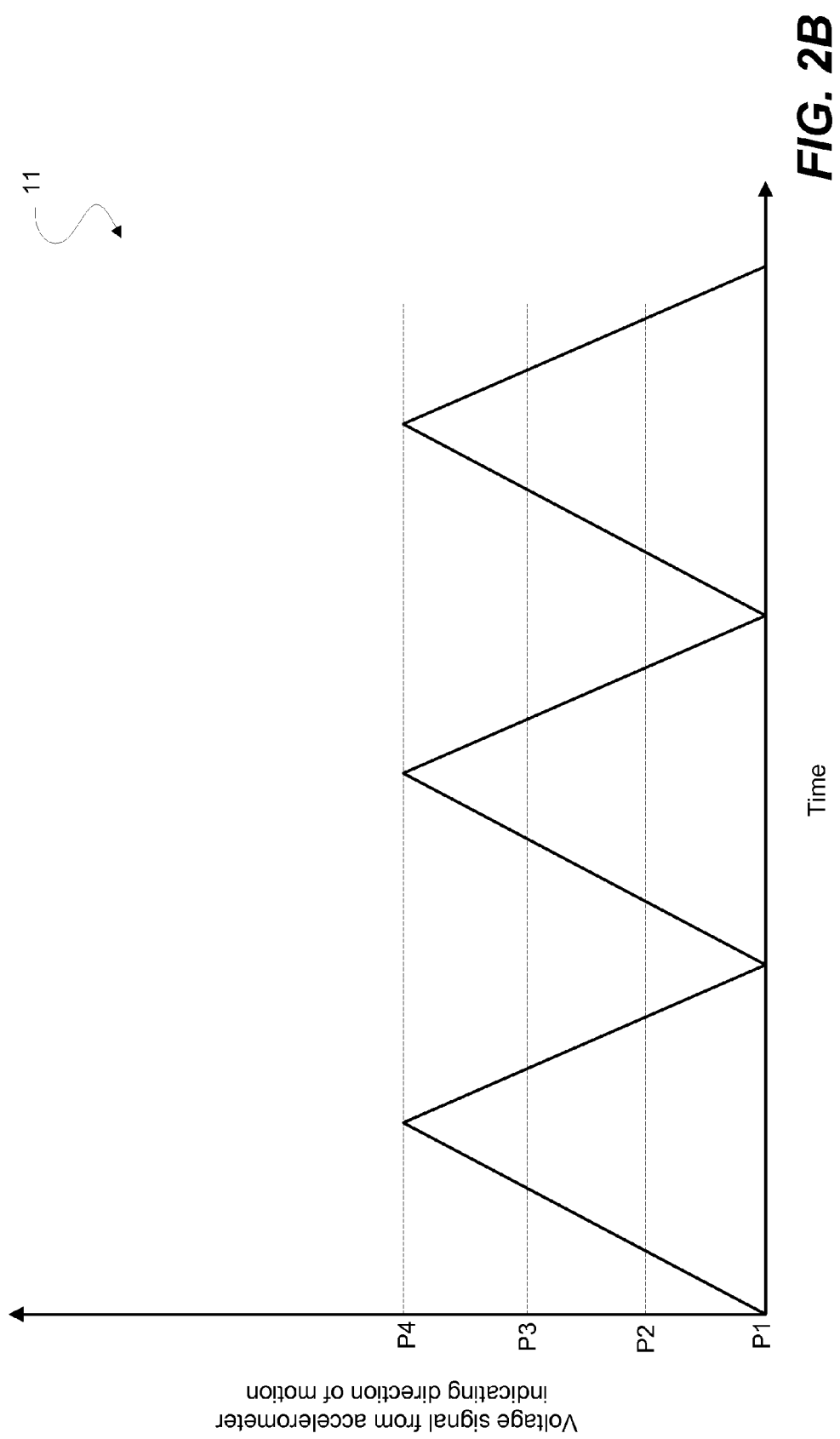
FIG. 2B is a graph illustrating an exemplary single axis output from an accelerometer sensor in the sensor package depicted in the FIG. 2A illustration.

FIG. 2B is a graph 11 illustrating an exemplary single axis output from an accelerometer sensor 159 in the sensor package 125 depicted in the FIG. 2A illustration. As the arm of the runner translates back and forth between and through positions P1 through P4, a single axis graph generated by double axis, or triple axis, accelerometer 159 may be generated similar to the graph 11. Notably, as the graph 11 indicates that the sensor package 125 is at either position P1 or P4, the CTM embodiment may recognize that noise attributable to a motion artifact is at a minimum. Based on such recognition the CTM embodiment may trigger a reading from a pulse oximeter, or other sensor, included in the sensors 159 of the sensor package 125.

Similarly, a CTM embodiment may track an accelerometer graph, such as exemplary graph 11 while simultaneously taking readings from a pulse oximeter and/or other sensors 159 in the sensor package 125. The entire collected data may be stored and compared to determine which of the pulse oximeter readings is associated with a time stamp that is simultaneous with, or nearly simultaneous with, either of points P1 and P4. Other methods for leveraging an accelerometer reading to optimize when to take and/or consider a reading from a different sensor 159 package are envisioned and fall within the scope of a CTM embodiment.

Figure 3:
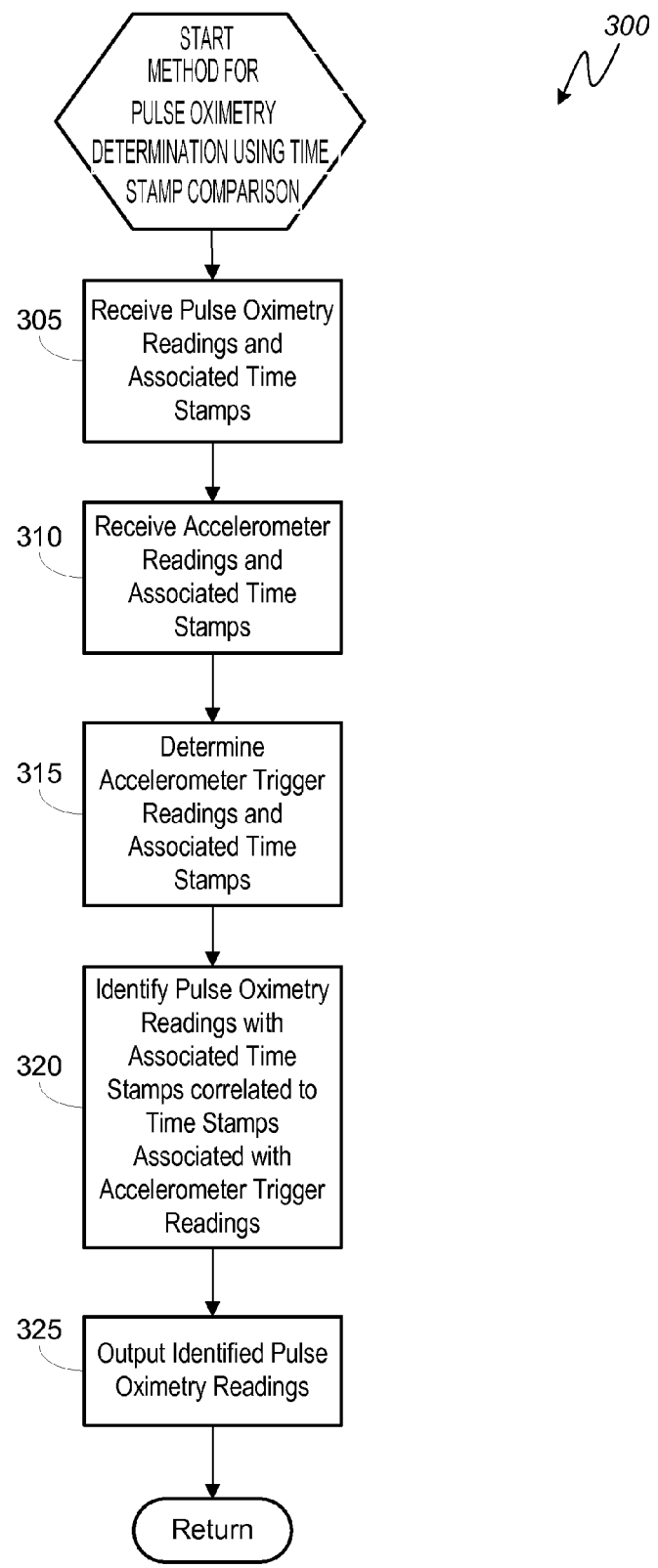
FIG. 3 is a logical flowchart illustrating a continuous transdermal monitoring ("CTM") method for pulse oximetry determination using time stamp comparison.

FIG. 3 is a logical flowchart illustrating a continuous transdermal monitoring ("CTM") method 300 for pulse oximetry determination using time stamp comparison. Beginning at block 305, pulse oximetry readings from a pulse oximeter 159 in sensor package 125 may be received continuously along with time stamps indicating when the various readings were taken. At block 310, an accelerometer 159 may be continuously monitored to generate a graph or graphs indicative of motion of the sensor package 125, such as may be correlated to the "swinging" back and forth of a runner's arm. Notably, and as would be understood by one of ordinary skill in the art of accelerometers, an accelerometer may be operable to detect motion in multiple axises which may be combined to identify points of minimal motion.

Next, at block 315 the accelerometer readings may be parsed to identify which readings are indicative of minimal motion of the sensor package. The identified readings may be considered "trigger readings" for triggering the subsequent identification of pulse oximetry readings at block 320. Notably, the time stamps associated with the accelerometer trigger readings at block 315 may be used by the CTM embodiment to identify which of the pulse oximetry readings were taken at times associated with minimal motion artifact. At block 325, the identified pulse oximetry readings may be output to the user and/or stored for later query. The method 300 returns.

Figure 4:
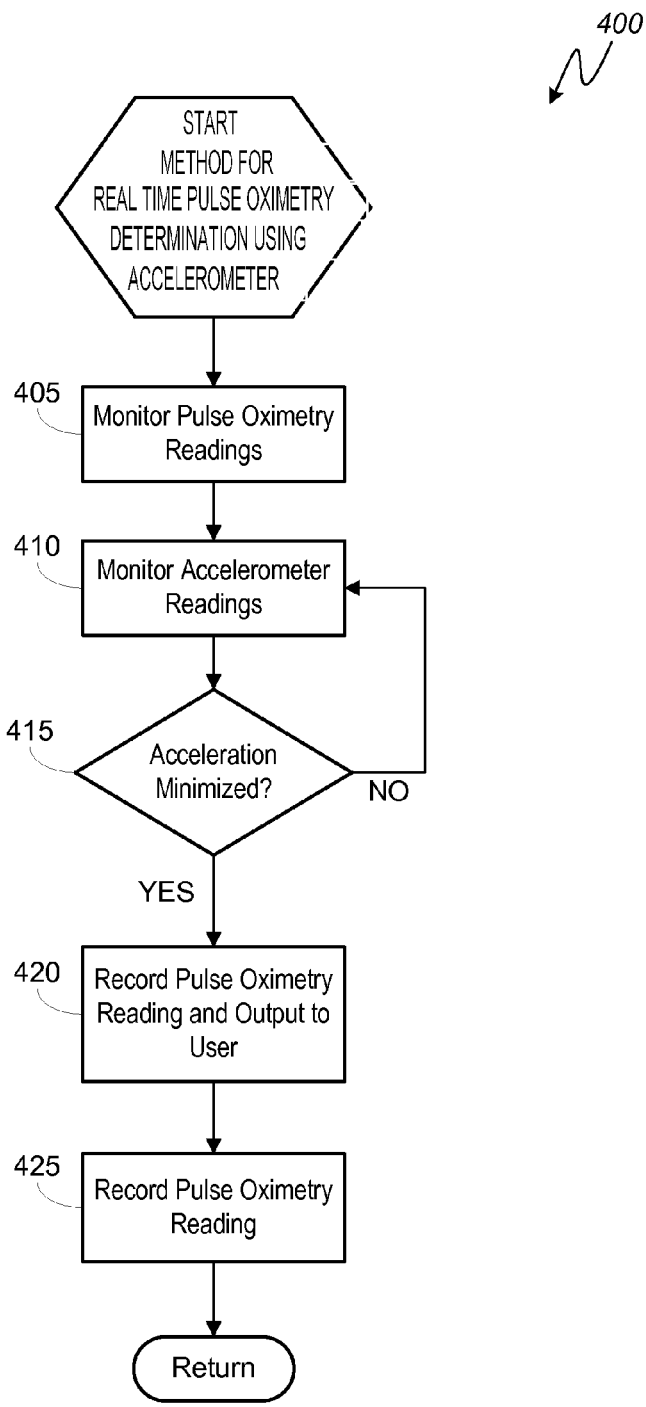
FIG. 4 is a logical flowchart illustrating a continuous transdermal monitoring ("CTM") method for near real time pulse oximetry determination based on accelerometer readings.

FIG. 4 is a logical flowchart illustrating a continuous transdermal monitoring ("CTM") method 400 for near real time pulse oximetry determination based on accelerometer readings. Beginning at block 405, pulse oximetry readings generated by a pulse oximeter sensor 159 may be monitored. Simultaneously, at block 410 an accelerometer in the sensors 159 may be monitored. Next, at decision block 415, if the monitored accelerometer readings indicate that acceleration motion is minimized, then the CTM embodiment may determine that the sensor package is momentarily stationary such that any noise attributable to motion artifact is minimized. If acceleration is not minimized, the "no" branch is followed back to block 410 and the accelerometer readings are continued to be monitored.

If, however, the accelerometer readings indicated that motion of the sensor package is minimized, then the "yes" branch is followed to block 420 and the pulse oximetry reading is recorded. At block 425, the pulse oximetry reading, which may be accurate due to the fact that it was taken at a time that motion artifact was minimized, may be output to the user and/or stored for later query. The method 400 returns.

Figure 5:
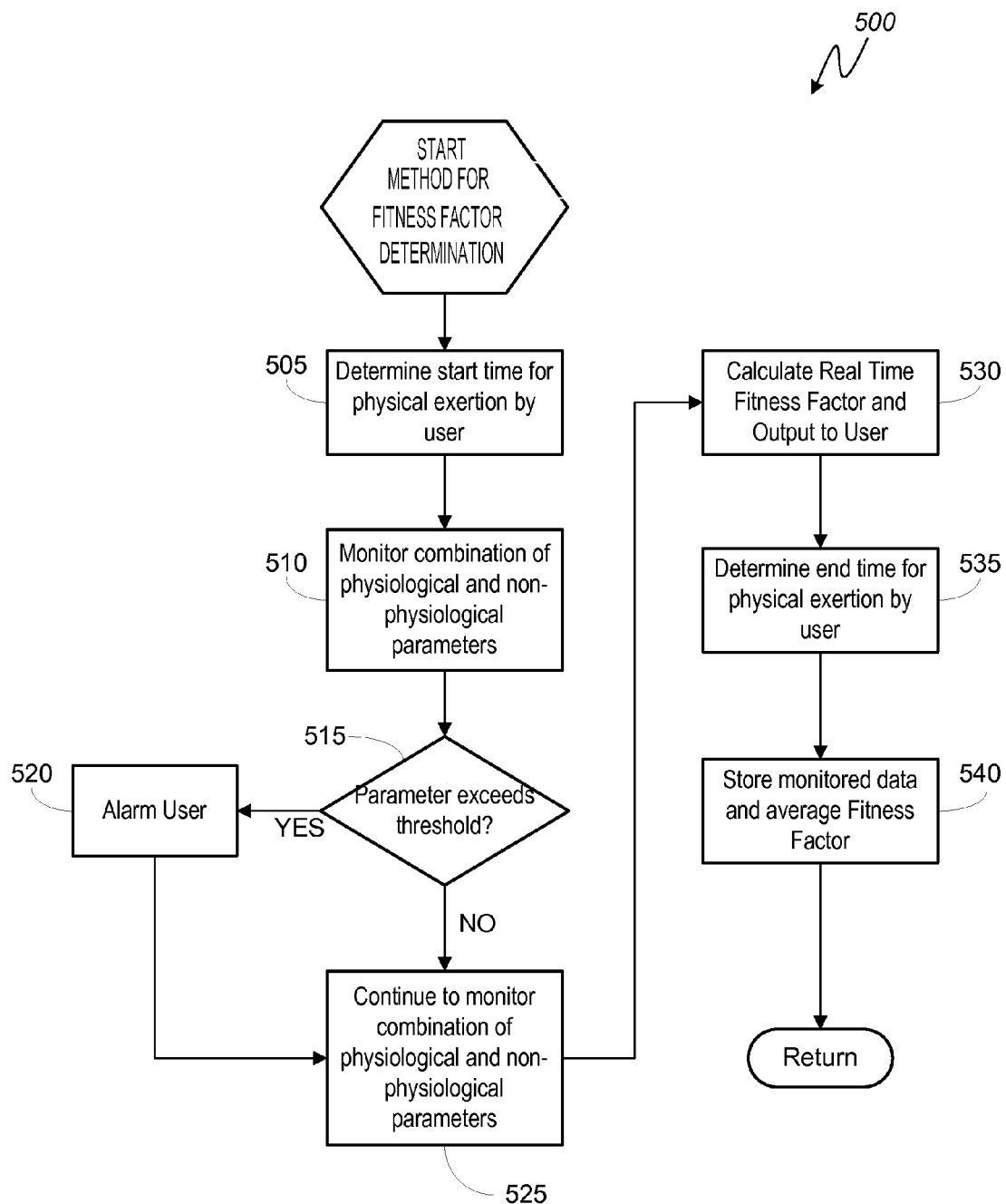
FIG. 5 is a logical flowchart illustrating a continuous transdermal monitoring ("CTM") method for generating a fitness factor output.

FIG. 5 is a logical flowchart illustrating a continuous transdermal monitoring ("CTM") method 500 for generating a fitness factor output. Beginning at block 505, a start time for a duration of physical exertion by a user may be recognized. Beginning with the start time, and throughout the duration, at block 510 one or more sensor readings indicative of physiological and/or non-physiological parameters may be monitored and tracked. At decision block 515, if any one or more of the parameters exceeds a predetermined threshold, such as for example a heart pulse rate in excess of 200 beats per minutes, then the "yes" branch may be followed to block 520 and the user alarmed. The alarm may be presented via the sensor package 125, such as through an LED display or audible tone, or through a hub component 100 in a similar manner.

Returning to the method 500, if a parameter threshold has not been exceeded, or if no parameter thresholds are set, then the "no" branch is followed to block 525 and the various parameters are continuously monitored.

Subsequently, at block 530, a real time fitness factor, generated by a FF module 101, may be output to the user. As described above, the fitness factor may be the output of a CTM algorithm that weights certain combinations of the parameters monitored and tracked by the CTM embodiment. Notably, it is envisioned that a CTM algorithm for generating a fitness factor may be customizable by the user in some embodiments. At block 535, the end time for the duration of physical exertion may be determined. Subsequently, at block 540 the various parameter data monitored during the exercise period and tracked by the CTM embodiment may be output to the user and/or stored for later query. The method 500 returns.

Figure 6:
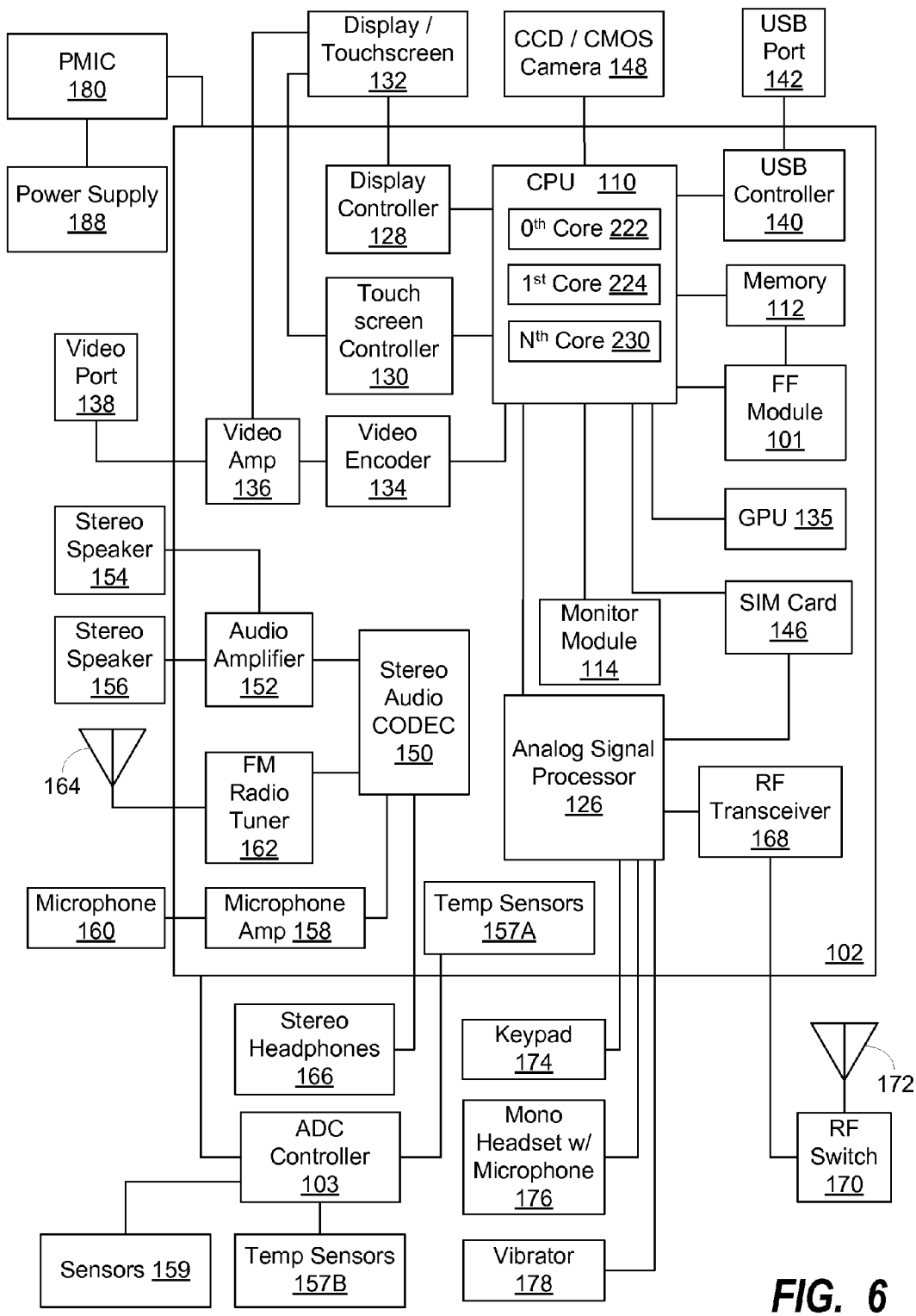
FIG. 6 is a functional block diagram illustrating an exemplary, non-limiting aspect of a portable computing device ("PCD") in the form of a wireless telephone for implementing continuous transdermal monitoring ("CTM") methods and systems.

FIG. 6 is a functional block diagram illustrating an exemplary, non-limiting aspect of a portable computing device ("PCD"), such as a hub component 100 and/or a sensor package 125, for implementing continuous transdermal monitoring ("CTM") methods and systems. The PCD may be in the form of a wireless telephone in some CTM embodiments. As shown, the PCD 100, 125 includes an on-chip system 102 that includes a multi-core central processing unit ("CPU") 110 and an analog signal processor 126 that are coupled together. The CPU 110 may comprise a zeroth core 222, a first core 224, and an Nth core 230 as understood by one of ordinary skill in the art. Further, instead of a CPU 110, a digital signal processor ("DSP") may also be employed as understood by one of ordinary skill in the art.

In general, fitness factor ("FF") module 101 may be formed from hardware and/or firmware and may be responsible for determining when certain sensor readings should be taken and calculating a fitness factor according to one or more fitness factor algorithms. It is envisioned that fitness factor algorithms in some CTM embodiments may be customizable by a user.

As illustrated in FIG. 6, a display controller 128 and a touch screen controller 130 are coupled to the digital signal processor 110. A touch screen display 132 external to the on-chip system 102 is coupled to the display controller 128 and the touch screen controller 130. PCD 100, 125 may further include a video encoder 134, e.g., a phase-alternating line ("PAL") encoder, a sequential couleur avec memoire ("SECAM") encoder, a national television system(s) committee ("NTSC") encoder or any other type of video encoder 134. The video encoder 134 is coupled to the multi-core CPU 110. A video amplifier 136 is coupled to the video encoder 134 and the touch screen display 132. A video port 138 is coupled to the video amplifier 136. As depicted in FIG. 6, a universal serial bus ("USB") controller 140 is coupled to the CPU 110. Also, a USB port 142 is coupled to the USB controller 140. A memory 112, which may include a PoP memory, a cache 116, a mask ROM/Boot ROM, a boot OTP memory, a DDR memory 115 may also be coupled to the CPU 110. A subscriber identity module ("SIM") card 146 may also be coupled to the CPU 110. Further, as shown in FIG. 6, a digital camera 148 may be coupled to the CPU 110. In an exemplary aspect, the digital camera 148 is a charge-coupled device ("CCD") camera or a complementary metal-oxide semiconductor ("CMOS") camera.

As further illustrated in FIG. 6, a stereo audio CODEC 150 may be coupled to the analog signal processor 126. Moreover, an audio amplifier 152 may be coupled to the stereo audio CODEC 150. In an exemplary aspect, a first stereo speaker 154 and a second stereo speaker 156 are coupled to the audio amplifier 152. FIG. 6 shows that a microphone amplifier 158 may be also coupled to the stereo audio CODEC 150. Additionally, a microphone 160 may be coupled to the microphone amplifier 158. In a particular aspect, a frequency modulation ("FM") radio tuner 162 may be coupled to the stereo audio CODEC 150. Also, an FM antenna 164 is coupled to the FM radio tuner 162. Further, stereo headphones 166 may be coupled to the stereo audio CODEC 150.

FIG. 6 further indicates that a radio frequency ("RF") transceiver 168 may be coupled to the analog signal processor 126. An RF switch 170 may be coupled to the RF transceiver 168 and an RF antenna 172. As shown in FIG. 6, a keypad 174 may be coupled to the analog signal processor 126. Also, a mono headset with a microphone 176 may be coupled to the analog signal processor 126. Further, a vibrator device 178 may be coupled to the analog signal processor 126. FIG. 6 also shows that a power supply 188, for example a battery, is coupled to the on-chip system 102 through a power management integrated circuit ("PMIC") 180. In a particular aspect, the power supply 188 includes a rechargeable DC battery or a DC power supply that is derived from an alternating current ("AC") to DC transformer that is connected to an AC power source. In another particular aspect, the power supply 188 includes a kinetically rechargeable DC battery.

The CPU 110 may also be coupled to one or more internal, on-chip thermal sensors 157A as well as one or more external, off-chip thermal sensors 157B and physiological sensors 159. The on-chip thermal sensors 157A may comprise one or more proportional to absolute temperature ("PTAT") temperature sensors that are based on vertical PNP structure and are usually dedicated to complementary metal oxide semiconductor ("CMOS") very large-scale integration ("VLSI") circuits. The off-chip thermal sensors 157B may comprise one or more thermistors. The thermal sensors 157 may produce a voltage drop that is converted to digital signals with an analog-to-digital converter ("ADC") controller (not shown). However, other types of thermal sensors 157 may be employed. The physiological sensors 159 may include, but are not limited to including, a pulse oximeter, a co-oximeter, a core body temperature sensor, a pulse rate sensor, an accelerometer, etc.

The touch screen display 132, the video port 138, the USB port 142, the camera 148, the first stereo speaker 154, the second stereo speaker 156, the microphone 160, the FM antenna 164, the stereo headphones 166, the RF switch 170, the RF antenna 172, the keypad 174, the mono headset 176, the vibrator 178, thermal sensors 157B, physiological sensors 159, the PMIC 180 and the power supply 188 are external to the on-chip system 102. It will be understood, however, that one or more of these devices depicted as external to the on-chip system 102 in the exemplary embodiment of a PCD 100, 125 in FIG. 6 may reside on chip 102 in other exemplary embodiments.

In a particular aspect, one or more of the method steps described herein may be implemented by executable instructions and parameters stored in the memory 112 or as form the FF module 101. Further, the FF module 101, the memory 112, the instructions stored therein, or a combination thereof may serve as a means for performing one or more of the method steps described herein.

Figure 7:
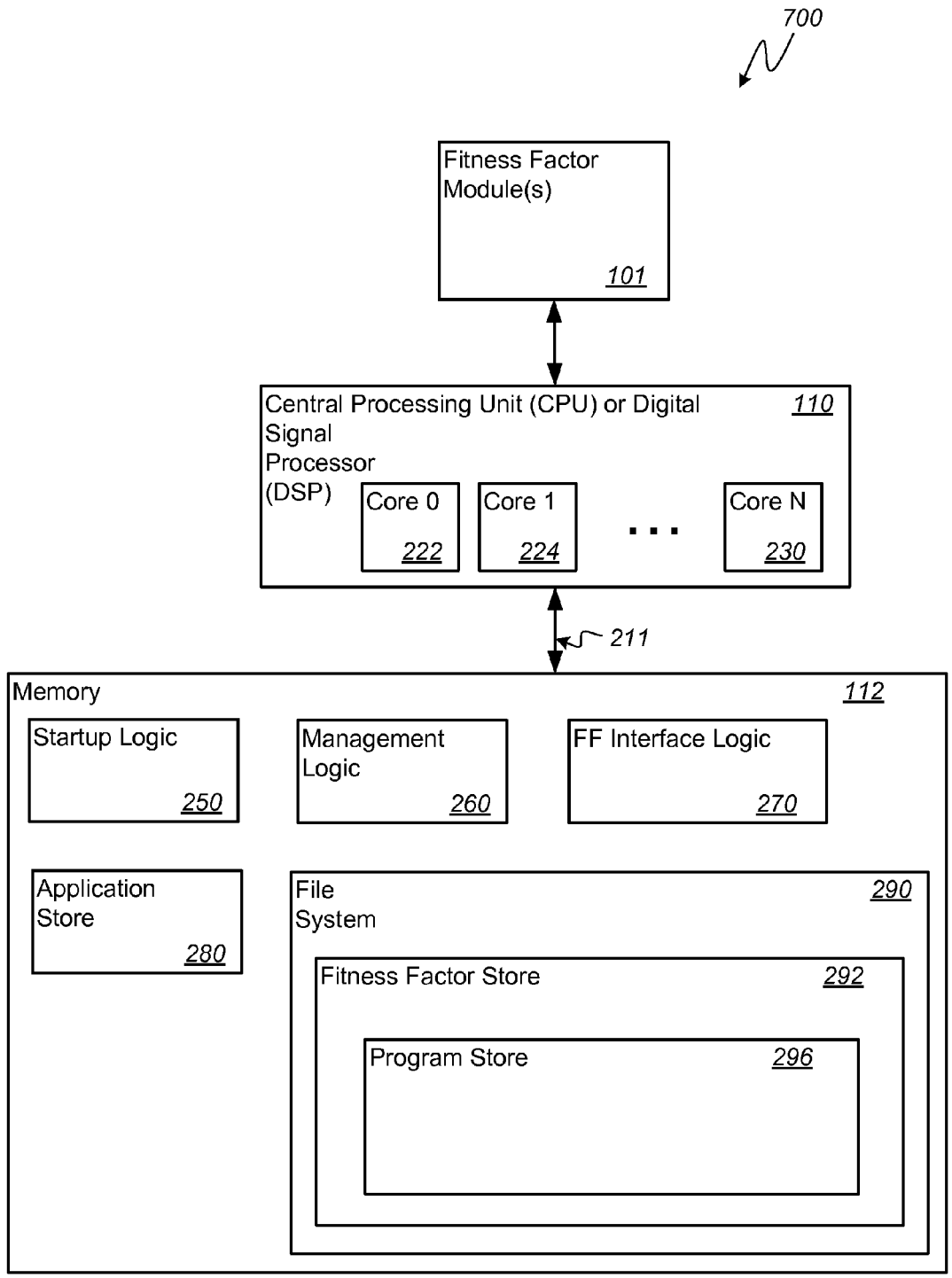
FIG. 7 is a schematic diagram illustrating an exemplary software architecture for continuous transdermal monitoring ("CTM") embodiments.

FIG. 7 is a schematic diagram illustrating an exemplary software architecture 700 for continuous transdermal monitoring ("CTM") embodiments. As illustrated in FIG. 7, the CPU or digital signal processor 110 is coupled to the memory 112 via main bus 211. The memory 112 may reside within a hub component 100, a sensor package 125 or a combination thereof. Similarly, it will be understood that the FF module 101 and the CPU 110 may reside within a hub component 100, a sensor package 125 or a combination thereof.

The CPU 110, as noted above, is a multiple-core processor having N core processors. That is, the CPU 110 includes a first core 222, a second core 224, and an $N^{th}$ core 230. As is known to one of ordinary skill in the art, each of the first core 222, the second core 224 and the $N^{th}$ core 230 are available for supporting a dedicated application or program. Alternatively, one or more applications or programs may be distributed for processing across two or more of the available cores.

The CPU 110 may receive commands from the fitness factor module(s) 101 that may comprise software and/or hardware. If embodied as software, the module(s) 101 comprise instructions that are executed by the CPU 110 that issues commands to other application programs being executed by the CPU 110 and other processors.

The first core 222, the second core 224 through to the Nth core 230 of the CPU 110 may be integrated on a single integrated circuit die, or they may be integrated or coupled on separate dies in a multiple-circuit package. Designers may couple the first core 222, the second core 224 through to the $N^{th}$ core 230 via one or more shared caches and they may implement message or instruction passing via network topologies such as bus, ring, mesh and crossbar topologies.

Bus 211 may include multiple communication paths via one or more wired or wireless connections, as is known in the art and described above in the definitions. The bus 211 may have additional elements, which are omitted for simplicity, such as controllers, buffers (caches), drivers, repeaters, and receivers, to enable communications. Further, the bus 211 may include address, control, and/or data connections to enable appropriate communications among the aforementioned components.

When the logic used by the PCD 100, 125 is implemented in software, as is shown in FIG. 7, it should be noted that one or more of startup logic 250, management logic 260, FF interface logic 270, applications in application store 280 and portions of the file system 290 may be stored on any computer-readable medium for use by, or in connection with, any computer-related system or method. In the context of this document, a computer-readable medium is an electronic, magnetic, optical, or other physical device or means that can contain or store a computer program and data for use by or in connection with a computer-related system or method. The various logic elements and data stores may be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer-readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random-access memory (RAM) (electronic), a read-only memory (ROM) (electronic), an erasable programmable read-only memory (EPROM, EEPROM, or Flash memory) (electronic), an optical fiber (optical), Flash, and a portable compact disc read-only memory (CDROM) (optical). Note that the computer-readable medium could even be paper or another suitable medium upon which the program is printed, as the program can be electronically captured, for instance via optical scanning of the paper or other medium, then compiled, interpreted or otherwise processed in a suitable manner if necessary, and then stored in a computer memory.

In an alternative embodiment, where one or more of the startup logic 250, management logic 260 and perhaps the FF interface logic 270 are implemented in hardware, the various logic may be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The memory 112 is a non-volatile data storage device such as a flash memory or a solid-state memory device. Although depicted as a single device, the memory 112 may be a distributed memory device with separate data stores coupled to the digital signal processor 110 (or additional processor cores).

The startup logic 250 includes one or more executable instructions for selectively identifying, loading, and executing a select program for identifying accurate physiological sensor readings and/or generating a fitness factor. The startup logic 250 may identify, load and execute a select FF program. An exemplary select program may be found in the program store 296 of the embedded file system 290. The exemplary select program, when executed by one or more of the core processors in the CPU 110 may operate in accordance with one or more signals provided by the FF module 101 to identify accurate physiological sensor readings and/or generate a fitness factor.

The management logic 260 includes one or more executable instructions for terminating a CTM program on one or more of the respective processor cores, as well as selectively identifying, loading, and executing a more suitable replacement program. The management logic 260 is arranged to perform these functions at run time or while the PCD 100 is powered and in use by an operator of the device. A replacement program, which may be customized by a user in some CTM embodiments, may be found in the program store 296 of the embedded file system 290.

The interface logic 270 includes one or more executable instructions for presenting, managing and interacting with external inputs to observe, configure, or otherwise update information stored in the embedded file system 290. In one embodiment, the interface logic 270 may operate in conjunction with manufacturer inputs received via the USB port 142. These inputs may include one or more programs to be deleted from or added to the program store 296. Alternatively, the inputs may include edits or changes to one or more of the programs in the program store 296. Moreover, the inputs may identify one or more changes to, or entire replacements of one or both of the startup logic 250 and the management logic 260. By way of example, the inputs may include a change to the weight of parameters used to generate a customized fitness factor.

The interface logic 270 enables a manufacturer to controllably configure and adjust an end user's experience under defined operating conditions on the PCD 100. When the memory 112 is a flash memory, one or more of the startup logic 250, the management logic 260, the interface logic 270, the application programs in the application store 280 or information in the embedded file system 290 may be edited, replaced, or otherwise modified. In some embodiments, the interface logic 270 may permit an end user or operator of the PCD 100, 125 to search, locate, modify or replace the startup logic 250, the management logic 260, applications in the application store 280 and information in the embedded file system 290. The operator may use the resulting interface to make changes that will be implemented upon the next startup of the PCD 100, 125. Alternatively, the operator may use the resulting interface to make changes that are implemented during run time.

The embedded file system 290 includes a hierarchically arranged fitness factor store 292. In this regard, the file system 290 may include a reserved section of its total file system capacity for the storage of information for the configuration and management of the various fitness factor and/or CTM algorithms used by the PCD 100, 125.

Certain steps in the processes or process flows described in this specification naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Additionally, one of ordinary skill in programming is able to write computer code or identify appropriate hardware and/or circuits to implement the disclosed invention without difficulty based on the flow charts and associated description in this specification, for example. Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the drawings, which may illustrate various process flows.

In one or more exemplary aspects, the functions described may be implemented in hardware, software, firmware, or any combination thereof. If implemented in software, the functions may be stored on or transmitted as one or more instructions or code on a computer-readable medium. Computer-readable media include both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Therefore, although selected aspects have been illustrated and described in detail, it will be understood that various substitutions and alterations may be made therein without departing from the spirit and scope of the present invention, as defined by the following claims.

What is claimed is:

1. A method for minimizing the effects of motion artifact on sensor readings taken during continuous transdermal monitoring of a body part in motion, the method comprising:
    monitoring, with a processor, an output signal from an accelerometer, wherein the output signal indicates acceleration and deceleration of the body part of a user as the body part is in motion;
    determining, with the processor, from the output signal that the body part of the user has decelerated to a predetermined minimum before becoming momentarily stationary to begin acceleration;
    based on the determination that the body part of the user has decelerated to the predetermined minimum, determining, with the processor, a plurality of readings from a sensor, wherein determining the plurality of readings from the sensor occurs over a time window that includes the body part of the user becoming momentarily stationary; and
    recording in a memory device the determined plurality of readings from the sensor.

2. The method of claim 1, further comprising rendering an average of the determined plurality of readings from the sensor to the user via a display.

3. The method of claim 1, wherein the sensor is a pulse oximeter configured to:
    pulse a red light source for approximately 50 microseconds; and
    delay approximately 450 microseconds before pulsing an infrared light source approximately 50 microseconds.

4. The method of claim 3, wherein the plurality of readings from the pulse oximeter indicates a blood oxygen saturation level of the user.

5. The method of claim 3, wherein the pulse oximeter is a reflective pulse oximeter.

6. The method of claim 1, wherein the accelerometer is a 3-axis accelerometer.

7. The method of claim 1, wherein the body part of the user is a wrist.

8. A system for minimizing the effects of motion artifact on sensor readings taken during continuous transdermal monitoring of a body part in motion, the system comprising:
    a sensor package comprising a processor, an accelerometer, a sensor and a memory device, the sensor package configured to:
        monitor an output signal from the accelerometer, wherein the output signal indicates acceleration and deceleration of the body part of a user as the body part is in motion;
        determine from the output signal that the body part of the user has decelerated to a predetermined minimum before becoming momentarily stationary to begin acceleration;
        based on the determination that the body part of the user has decelerated to the predetermined minimum, determine a plurality of readings from the sensor, wherein the determined plurality of readings from the sensor occurs over a time window that includes the body part of the user becoming momentarily stationary; and
        record the determined plurality of readings from the pulse oximeter in the memory device.

9. The system of claim 8, further comprising a hub device configured to render an average of the determined plurality of readings from the sensor to the user via a display.

10. The system of claim 8, wherein the sensor is a pulse oximeter configured to:

pulse a red light source for approximately 50 microseconds; and delay approximately 450 microseconds before pulsing an infrared light source approximately 50 microseconds.

11. The system of claim 10, wherein the plurality of readings from the pulse oximeter indicate a blood oxygen saturation level of the user.

12. The system of claim 10, wherein the pulse oximeter is a reflective pulse oximeter.

13. The system of claim 8, wherein the accelerometer is a 3-axis accelerometer.

14. The system of claim 8, wherein the body part of the user is a wrist.

15. A computer program product comprising a non-transitory computer usable medium having a computer readable program code embodied therein, said computer readable program code adapted to be executed by a processor and cause the processor to implement a method for minimizing the effects of motion artifact on sensor readings taken during continuous transdermal monitoring of a body part in motion, said method comprising:

monitoring an output signal from an accelerometer, wherein the output signal indicates acceleration and deceleration of the body part of a user as the body part is in motion;

determining from the output signal that the body part of the user has decelerated to a predetermined minimum before becoming momentarily stationary to begin acceleration;

based on the determination that the body part of the user has decelerated to the predetermined minimum, determining a plurality of readings from a sensor, wherein determining the plurality of readings from the sensor occurs over a time window that includes the body part of the user becoming momentarily stationary; and recording in a memory device the determined plurality of readings from the sensor.

16. The computer program product of claim 15, further comprising rendering an average of the determined plurality of readings from the sensor to the user via a display.

17. The computer program product of claim 15, wherein the sensor is a pulse oximeter configured to:

pulse a red light source for approximately 50 microseconds; and delay approximately 450 microseconds before pulsing an infrared light source approximately 50 microseconds.

18. The computer program product of claim 17, wherein the plurality of readings from the pulse oximeter indicates a blood oxygen saturation level of the user.

19. The computer program product of claim 17, wherein the pulse oximeter is a reflective pulse oximeter.

20. The computer program product of claim 15, wherein the accelerometer is a 3-axis accelerometer.

* * * * *